United States Patent [19]

Penneck

[11] 3,969,308

[45] July 13, 1976

[54] POLYMER COMPOSITIONS

[75] Inventor: Richard John Penneck, Lechlade, England

[73] Assignee: Raychem Limited, London, England

[22] Filed: Jan. 13, 1975

[21] Appl. No.: 540,447

Related U.S. Application Data

[63] Continuation-in-part of Ser. No. 273,991, July 21, 1972, abandoned.

[52] U.S. Cl. .......................... 260/37 SB; 260/824 R; 260/824 EP; 260/827
[51] Int. Cl.² ........................................ C08L 83/04
[58] Field of Search ...... 260/37 SB, 824 R, 824 EP, 260/827

[56] References Cited
UNITED STATES PATENTS

| | | | |
|---|---|---|---|
| 2,859,198 | 11/1958 | Sears et al. ...................... | 260/37 SB |
| 2,867,603 | 1/1959 | Safford et al. ................ | 260/37 SB X |
| 2,888,419 | 5/1959 | Safford ........................ | 260/37 SB X |
| 2,993,809 | 7/1961 | Bueche et al. ............. | 260/37 SB UX |
| 3,079,361 | 2/1963 | Plueddemann .............. | 260/37 SB X |
| 3,290,165 | 12/1966 | Iannicelli .................. | 260/37 SB UX |
| 3,326,869 | 6/1967 | Perrone ....................... | 260/37 SB X |
| 3,341,490 | 9/1967 | Burdick et al. .................. | 260/37 SB |
| 3,538,028 | 11/1970 | Morgan ....................... | 260/37 SB X |

Primary Examiner—Lewis T. Jacobs
Attorney, Agent, or Firm—Lyon & Lyon

[57] ABSTRACT

A novel composition is disclosed which contains a silicone polymer, a non-silicone polymer other than polytetrafluoroethylene and a chemically treated filler. The non-silicone polymer may be an elastomer or a thermoplastic such as a polyolefin, a copolymer containing an olefin, a halogen-containing polymer or copolymer or a copolymer of fluorine-containing polymers other than polytetrafluoroethylene. The filler is an inorganic silicon-containing compound having a surface area of at least 40 square meters per gram which has been treated with a substituted silane. The treated filler is first blended with the non-silicone polymer and this compound is then mixed with the silicone polymer.

5 Claims, No Drawings

POLYMER COMPOSITIONS

This is a continuation-in-part of application Ser. No. 273991 filed July 21, 1972 and now abandoned.

Silicone rubbers have a unique combination of properties, possessing most of the characteristics of natural and synthetic elastomers in addition to outstanding resistance to exposure at high and low temperatures. Silicone rubbers can remain flexible at temperatures as low as −100°C yet perform satisfactorily at temperatures as high as 200°C. Their electrical properties such as electric strength, power factor and permittivity are good and are retained at elevated temperatures. The resistance to ozone and corona discharge is excellent. Thus silicone rubbers find commercial use in, for example, gaskets, O-rings, oil seals, wire and cable insulation, and hose and tubing.

The usefulness of silicone rubbers was extended by the discovery disclosed in British Patent Specification No. 1,010,064, that they could be made heat-recoverable by the incorporation of a crystalline polymer and co-crosslinking of the rubber and the crystalline polymer, the crosslinking being effected, for example, by high energy radiation, for example by β- or γ- rays, or by chemical means, for example by the use of peroxides. After crosslinking, the material is heated above the crystalline melting point, distorted, for example, expanded, and cooled while the distorted state is maintained. The material can be caused to recover towards its original form by brief heating at a temperature above the distortion temperature.

Further uses may be found for silicone rubbers by blending with them a fluoro-olefin polymer, for example a copolymer of vinylidene fluoride with hexafluoropropylene or 1-hydropentafluoropropene, thus giving better chemical and heat resistance, or by the incorporation of polytetrafluoroethylene to improve the tear resistance, oil resistance and compression set properties.

However, the blending of any non-silicone polymer with a silicone polymer is extremely difficult and usually results in distortion or phase separation on manufacturing articles from the polymer blend. When the manufacturing step is moulding, for example by compression, transfer or injection, or extrusion, phase separation is usually a severe problem and lamination occurs. This lamination often manifests itself by the appearance of a fibrous network. In the case of heat-shrinkable silicone-based materials which contain a crystalline polyolefin, for example polyethylene, or a crystalline fluorinated polymer, for example polyvinylidene fluoride, the phase separation is not so severe as to cause lamination, but nevertheless is still a problem because it impairs the heat shrinkability or elastic memory of an expanded heat-recoverable article; the expanded article tends to "creep" back towards the unexpanded form. The usefulness of an expanded article is therefore diminished as the size decreases on storage. In some instances this creep-back may be as high as 50 %. In addition to the disadvantages outlined above, the tensile strength of blends of silicone polymers with non-silicone polymers made by previously proposed methods is often very low, typically 600 psi.

The present invention provides a composition comprising a silicone polymer, a non-silicone polymer other than polytetrafluoroethylene and a chemically treated filler, the chemically treated filler being a filler comprising an inorganic silicon-containing compound containing the Si—O—Si group and having a specific surface area (measured by the BET method) of at least 40 $m^2/g$. which filler has been treated with one or more silanes having bonded to the or each silicon atom at least one organic group bonding through a Si—C bond. The invention also provides a composition comprising a silicone polymer, a non-silicone polymer, and a chemically treated filler, the chemically treated filler being a filler comprising an inorganic silicon-containing compound containing the Si—O—Si group and having a specific surface area (measured by the BET method) of at least 40 $m^2/g$, which filler has been treated with one or more silanes, the composition having been produced by blending the silicone polymer with a blend of the non-silicone polymer and the chemically treated filler.

In the composition of the invention, the silicone polymer and/or the non-silicone polymer is advantageously a thermoplastic or elastomeric polymer. For electrical uses, the silicone polymer is preferably elastomeric. The proportion of the silicone polymer in the composition is advantageously more than 10 % by weight of the total polymer content and is preferably at least 20 % by weight of the total polymer content, viz. at least 20 % by weight silicone polymer, the remaining polymer being the non-silicone polymer or polymers previously referred to. In some cases it may be advantageous for the proportion of silicone polymer to be greater than 50 % by weight of the total polymer content. The compositions of the invention may, of course, contain more than one non-silicone polymer and/or more than one silicone polymer.

The invention also provides a process for the manufacture of a composition, which process comprises blending together a silicone polymer, a non-silicone polymer other than polytetrafluoroethylene, a filler comprising an inorganic silicone-containing compound containing the Si—O—Si group and having a specific surface area (measured by the BET method) of at least 40 $m^2/g$, and one or more silanes having bonded to the or each silicon atom at least one organic group bonding through a Si-C bond. The invention further provides a process for blending one or more silicone polymers with one or more non-silicone polymers which comprises a. blending the non-silicone polymer or polymers with a filler comprising an inorganic silicon compound containing the Si—O—Si group, the filler having a specific surface area (as measured by the BET method) of at least 40 $m^2/g$, and one or more silanes, the filler and the silane(s) having bonded to the or each silicon atom at least one organic group bonding through a Si-C bond forming a chemically treated filler, and b. blending the blend obtained from (a) with the silicone polymer or polymers.

In the compositions of the invention, particularly in in those prepared by blending the silicone polymer with a blend of the chemically treated filler and the non-silicone polymer, phase separation on extrusion and moulding is very greatly reduced and, in some cases, completely eliminated. It is believed that the chemically treated fillers, which are highly compatible with both silicone polymers and non-silicone polymers, act rather like surface active agents and result in increased compatibility of the two phases. However, it is to be understood that the scope of the invention is in no way to be limited by the lack of an adequate theory to describe the phenomenon.

In some cases, the compositions of the invention also have improved electrical properties and high temperature properties compared with compositions which do not contain the chemically treated filler of the invention. In particular, the use of the chemically treated fillers may increase the useful lifetime of a polymer blend when the latter is subjected to high voltages in polluting conditons.

The treated fillers are employed in amounts sufficient to appreciably enhance compatibility of the silicone- and non-silicone polymer components of the blend. Preferably the compositions of the invention contain from about 5 to about 40 % by weight of treated filler, based on the combined weight of treated filler, silicone- and non-silicone polymers. Polymer blends contemplated for use in high voltage applications preferably contain from about 15 to about 40 % treated filler on a similar basis. As the art-skilled will appreciate from this disclosure, more treated filler may be employed in given instances, as where the silicone polymer intended for blending is not itself silicone filled, where to do so does not significantly embrittle or otherwise adversely affect the physical properties of the blended polymer composition.

The fillers which are used according to the invention are inorganic silicon compounds containing the Si—O—Si group and having a specific surface area (as measured by the nitrogen absorption metod of Brunauer, Emmett and Teller) of at least 40 m²/g, preferably at least 50 m²/g, and advantageously 100 to 300 m²/g. Other groups which may be present include the silanol Si—O—H group and reaction products of the silanol group with metal oxides or hydroxides, typical metals including calcium, magnesium, aluminium, zinc and boron. The fillers are suitably those silicas and silicates normally regarded as reinforcing fillers and having a specific surface area as measured by the nitrogen absorption method of Brunauer, Emmett and Teller (the so-called BET method) of at least 40 m²/g, preferably of at least 50 m²/g. The fillers may be classified as anhydrous, hydrated or aerogel fillers.

An anhydrous filler is usually defined as one containing less than 3.5 % bound water, whilst a hydrated filler contains more than this amount. The term "bound water" is defined as the ignition loss minus the 105°C drying weight loss. A correction is made for components other than water which may volatilize between 105°C and the temperature of ignition, which is usually 900° to 1100°C. An aerogel filler is defined solely with reference to the manufacturing process, which is discussed in more detail below.

The process for the manufacture of a typical anhydrous silica is to react silicon tetrachloride, hydrogen and oxygen at about 1000°C to produce anhydrous silica and hydrogen chloride, while hydrated silicas and silicates may be prepared by reacting a solution of sodium silicate with acids or metal salts. The addition of the salt or acid must be carefully controlled to give precipitation conditions favourable to the production of amorphous discrete particles. Typical silicates to be used in accordance with the present invention include those of calcium, aluminium and magnesium.

Aerogels, according to Bachman et al., Rubber Reviews 1959, issue of Rubber and Chemistry and Technology, are produced by replacing the water in a silica gel by an organic liquid, usually an alcohol, to form an organogel, heating this organogel in an autoclave above the critical temperature of the organic liquid so that no meniscus exists between the liquid and gaseous phases, and then venting the autoclave. This method removes the liquid phase without collapsing the gel.

In order to obtain the chemically treated fillers according to the present invention, one or more inorganic silicon compounds containing the Si—O—Si group is treated with one or more silanes. The silanes have bonded to the or each silicon atom at least one organic group bonding through a Si—C bond. The silane is advantageously a compound of the general formula $$R_nSiX_{4-n}$$

wherein $n$ represents 1, 2 or 3, R represents an organic group bonded to the silicon atom by a Si—C bond, and X represents a group or atom that is bonded to the silicon atom through an atom other than a carbon atom. When $n$ represents 2 or 3, the groups represented by R may be the same or different.

In a compound of the general formula $R_nSiX_{4-n}$, X may represent, for example, a halogen atom, preferably a chlorine atom, or a group of the formula —OR¹ in which R¹ may represent a hydrogen atom, or an alkyl group which preferably contains up to 4 carbon atoms.

The organic group represented by R in the above formula may be, for example, an alkyl or alkenyl radical preferably containing less than 6 carbon atoms, or aryl radical which may be unsubstituted or substituted, for example by one or more substituents selected from vinyl, methacryloxy, amino and mercapto groups.

Especially useful for use according to the invention are substituted silanes of the formulae:

$$R_1 R_2 R_3 Si Cl$$

$$R_1 R_2 Si Cl_2$$

$$R_1 Si Cl_3$$

$$R_4 Si (OR_5)_3$$

wherein each of $R_1$, $R_2$ and $R_3$ represents an alkyl, alkenyl or aryl group and may be the same or different, $R_4$ has the same meaning as $R_1$, but the groups represented by $R_4$ may be substituted, for example by a vinyl, methacryloxy, amino or mercapto group, $R_5$ represents a hydrogen atom or an alkyl group which contains up to 4 carbon atoms, preferably a methyl or ethyl group.

When the organic group in the silane which is bonded to the silicon atom by a Si—C bond contains one or more functional groups, such a group or groups may be treated with an organic compound which will react with one or more of the functional groups present. Reactions of this kind make possible the preparation of a wide variety of silanes, whose compatibility or reactivity with the polymers to be blended may be controlled by the choice of a suitable reactant. Examples of such reactions are as follows:

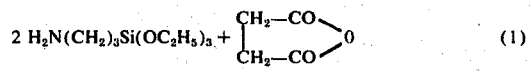

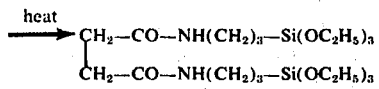

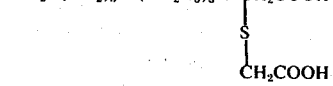

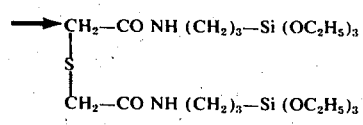

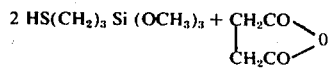

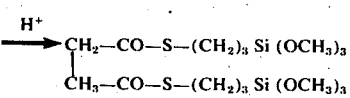

As silanes that may be used in the preparation of chemically treated fillers there may be mentioned, for example, dimethyl-dichlorosilane, methyl trichlorosilane, trimethyl chlorosilane, vinyl trichlorosilane, γ-methacryloxypropyl-trimethoxysilane and its hydrolysis products, N,N-bis(β-hydroxyethyl)-γ-aminopropyl-triethoxy silane and its hydrolysis products, vinyl triethoxysilane and its hydrolysis products, γ-glycidoxypropyl-trimethoxysilane, β-(3,4-epoxy cyclohexyl)-ethyl trimethoxy-silane γ-methacryloxypropyl-triethoxy silane and its hydrolysis products, γ-mercaptopropyl-trimethoxy silane and its hydrolysis products and vinyl trimethoxy silane. Preferred silanes are β-(3,4-epoxy cyclohexyl)-ethyl trimethoxy silane and γ-glycidoxy propyl trimethoxy silane.

The term "silanes" used in this specification is not intended to cover siloxanes.

The treatment of a filler with one or more silanes to obtain a chemically treated filler may be carried out in a number of ways. For example the filler may be subjected to a gaseous silane, for example, dimethyl dichlorosilane, at elevated temperatures, or the filler and silane may be mechanically mixed and the mixture stored until coating is complete, the time taken for the completion of the coating being in the range of one day to several weeks depending on the temperature. Alternatively, the non-silicone polymer and the untreated filler may be banded on a mill and the silane added on the mill. However, the method of treating the filler with the silane is not critical for the present invention. The filler is advantageously coated with the silane to the extent of one monolayer, although fillers of which a lower proportion of the surface is coated with silane may also be used in the process of the invention.

As non-silicone polymers which may be used in the composition of the present invention there may be mentioned polymers of which at least some of the structural units are derivable from an olefin, for example, ethylene, propylene, 1-butene, from an acrylate, for example ethyl acrylate or butyl acrylate, or from a methacrylate. Such polymers, which may be homo-, co- or ter-polymers, may also contain a relatively small number of structural units derivable from one or more other monomers, for example, vinyl acetate, dicyclopentadiene, 1,4-hexadiene and norbornadiene. Examples of especially useful non-silicone polymers are polyethylene, ethylene/propylene copolymers, ethylene/propylene/non-conjugated diene terpolymers (for example such a terpolymer in which the non-conjugated diene is 1,4-hexadiene, dicyclopentadiene or ethylidene norbornene), ethylene/methyl- or ethylacrylate copolymers, and ethylene/methyl methacrylate copolymers. An ethylene/methyl methacrylate copolymer suitably contains about 10 % by weight of methyl methacrylate and an ethylene/methyl acrylate copolymer may contain about 10 to 25 % by weight of methyl acrylate. Other suitable non-silicone polymers include butyl- or ethylacrylate/acrylonitrile copolymers, and chlorosulphonated polyolefins, for example chlorosulphonated low and high density polyethylene and chlorosulphonated polypropylenes.

Other non-silicone polymers which may be used include halogen- and hydrogen-containing polymers, especially fluorine-and hydrogen-containing polymers, a halogen- and hydrogen-containing polymer being a homopolymer of a polymerizable compound which contains at least one hydrogen atom and at least one halogen atom or a copolymer of (1) a compound which contains at least one halogen atom with (2) a compound which is copolymerizable with compound (1) and which contains at least one hydrogen atom if compound (1) does not contain hydrogen. One example of a halogen-and hydrogen-containing polymer is polyvinylidene chloride. As fluorine-containing olefins from which structural units in fluorine- and hydrogen-containing polymers may be derived there may be mentioned for example, vinyl fluoride, vinylidene fluoride, trifluoroethylene, hexafluoropropylene, tetrafluoroethylene, 1-hydropentafluoropropene. The non-silicone polymer may be, for example, a homo-, co- or ter-polymer of one or more of the abovementioned fluorine-containing olefins provided that at least one of the monomers from which the polymer is derived contains at least one hydrogen atom. Especially useful polymers include polyvinylidene fluoride, a copolymer of vinylidene fluoride with hexafluoropropylene, a copolymer of vinylidene fluoride and 1-hydropentafluoropropene, a terpolymer of vinylidene fluoride with hexafluoropropylene and tetrafluoroethylene, and a terpolymer of vinylidene fluoride with tetrefluoroethylene and 1-hydropentafluoropropene.

The compositions of the invention which include halogen-containing non-silicone polymers, generally have better solvent resistance than the silicone polymer alone and better low temperature properties than the halogen-containing polymer alone.

Among silicone polymers which may be used according to the present invention there may be mentioned polymers of which at least some of the structural units are derivable from, for example, dimethyl siloxane, methyl ethyl siloxane, methyl phenyl siloxane, methyl vinyl siloxane, methyl phenyl vinyl siloxane, phenyl vinyl siloxane, diphenyl siloxane, 3,3,3-trifluoropropyl methyl siloxane, silphenylene siloxane, β-cyanoethyl siloxane or γ-cyanopropyl siloxane. The silicone polymer may be, for example, a homopolymer or a copolymer of one or more of the above-mentioned siloxanes, and is advantageously polydimethyl siloxane or a copolymer of dimethyl siloxane with up to 5 % by weight, based on the weight of the dimethyl siloxane, of methyl vinyl siloxane. Other silicone polymers wich may be used include the carborane siloxanes. These are silicone-containing organo boron polymers some of which are described, for example, in British Patent Specifications Nos. 1,137,688 and 1,137,689 and in H. A.

Schroeder, "Carboranesiloxane polymers", Rubber Age, February, 1969. As used herein, the term silicone polymer(s) means polysiloxane(s).

The silicone polymer advantageously contains a filler; such a filler tends to improve the physical properties of the composition obtained. The filler may be, for example, a silica aerogel having a surface area of 100 to 380, preferably 150 to 250, $m^2/g$ (measured by the BET method) and having been treated with a siloxane (for example octamethyl tetrasiloxane) before being added to the silicone polymer. The coating is normally approximately one monolayer, and the treatment may be carried out cold or hot, with or without solvents. It appears that fillers treated by the hot process are better reinforcing materials.

In the process of the invention, the chemically treated filler is preferably blended with the non-silicone polymer and the mixture is then blended with the silicone polymer. In order to obtain the best physical properties, it is important to carry out the blending in this order: the especially advantageous results obtained when the process is performed in this way are not obtained when the chemically treated filler is blended with the silicone polymer first, although even with the latter order of blending a somewhat improved product will normally be obtained.

The compositions of the invention may also contain other ingredients, for example, fillers, pigments, stabilizers and free radical polymerization initiators. Examples of suitable additives are carbon blacks (but not for high voltage uses), ferric oxide, chromium oxide (including the hydrated version), alumina trihydrate, barium sulphate, cobalt oxide, cobalt aluminate, cobalt alumino-silicate, dibasic lead fumarate and dibasic lead phthalate. Among the free radical polymerization initiators that may be used there may be mentioned organic peroxides, for example, dicumyl peroxide, di-tertiary butyl peroxide; tertiary butylperbenzoate; 2,4-dichlorobenzoyl peroxide, 2,5-dimethyl-2,5-di(tertiary butylperoxy) hexane; and 2,5-dimethyl-2,5-di(tertiary butylperoxy) hexyne-3. The formulation may also contain co-curing agents, for example, polyfunctional vinyl or allyl compounds, for example, trimethylolpropane trimethacrylate, triallyl cyanurate, triallyl iso-cyanurate, pentaerythritol tetramethacrylate, allyl methacrylate, and ethylene glycol dimethacrylate.

A composition which contains a free radical polymerization initiator may be crosslinked merely by activating the initiator (by, for example, heating). If it is desired to crosslink a composition according to the invention without the use of chemical curing agents, this crosslinking may be effected by irradiation for example, with $\beta$- or $\gamma$-rays.

Shaped articles made from the composition of the invention may be used in a wide variety of ways, particularly if the composition is crosslinked. Such articles may include, if the non-silicone polymer is appropriate, heat-shrinkable tubing and moulded parts for the production of electrical harness systems and for the mechanical and electrical protection of cable joints.

As has been stated above, a number of the polymer compositions of the invention also have the valuable property of increased useful lifetime when subjected to high voltages in polluting conditions for example under dust or salt fog conditions. They are therefore useful for insulating electrical components and find particular use in sleeving for high voltage cables, for example 11 Kv cables, and as mouldings, for example, as sheds, which sheds may be heat-shrinkable. Sheds are devices which increase the electrical path length and therefore reduce the voltage gradient. They are used on transmission lines and also on the fibreglass "hot sticks" which are used by maintenance and construction gangs on live wire working. The use of sheds makes it possible to use short length poles in damp or polluting conditions without the danger of the operators obtaining electrical shocks; normally long poles, which would be unwieldy, would be required in order to obtain a suitable electrical path length. In addition, the sheds serve as a mechanical protection to the delicate surface of the poles. A further use of polymer compositions of the invention is in moulded form as stress cones at the ends of high voltage cables. Such stress cones can in some instances be heat-shrinkable.

Examples of compositions which are suitable for high voltage work are those in which the non-silicone polymer is a polyolefin, which polyolefin may be chlorosulphonated, or a copolymer of ethylene with various copolymerisable monomers. The silicone polymer in such a composition preferably contains no phenyl substitution. Preferred compositions are those in which the silicone polymer is a carborane siloxane, dimethyl siloxane, or a copolymer of dimethyl siloxane with up to 5 % by weight of methyl vinyl siloxane and the non-silicone polymer is high or low density polyethylene, an ethylene/propylene copolymer, an ethylene/propylene/non-conjugated diene terpolymer, an ethylene/methyl acrylate copolymer, an ethylene/ethyl acrylate copolymer, or an ethylene/methyl methacrylate copolymer. The non-conjugated diene is preferably 1,4-hexadiene, dicyclopentadiene or ethylidene norbornene.

Particularly suitable compositions include those in which polydimethyl siloxane or a carborane siloxane is blended with for example, a polyolefin, and those in which the non-silicone polymer is a blend of an ethylene/ethyl acrylate copolymer and low density polyethylene or a blend of an ethylene/ethyl acrylate copolymer and an ethylene/propylene/ethylidene norbornene terpolymer. The polydimethyl siloxane specified above may advantageously be replaced by a copolymer of dimethyl siloxane with a small percentage, for example less than 5 % by weight, of methyl vinyl siloxane.

The following Examples illustrate the invention:

EXAMPLE 1

20 grams of a low density polyethylene, melt index 3.0, were banded on a twin roll mill at 120°C. 10 grams of a coated silica filler were added and the polymer and filler were thoroughly mixed for about 15 minutes. The filler was a silica aerogel coated with dimethyl dichlorosilane to approximately one monolayer; the resultant filler had a specific surface area of approximately 150 sq. m/g (BET Method) and an average particle size of 20 m$\mu$.

70 grams of methyl phenyl vinyl siloxane polymer containing a reinforcing silica filler (Dow Corning DC 6565 U) were blended into the above mixture very thoroughly for 15 to 20 minutes and then 5 grams calcined ferric oxide (stabilizer) were added. The mill rolls were cooled to 80°C and 0.2 g of triallyl cyanurate and 0.1 g 2,5-dimethyl-2,5-di(tertiary butyl peroxy)-hexyne-3 were added and the whole mix milled for 2 minutes. The hide was then stripped from the mill and allowed to cool.

Test plaques 6 × 6 × 0.075 in. were pressed at 200°C for 15 minutes and the physical properties subsequently measured at 23°C. The results obtained are given in Table I.

Cylinders of internal diameter 0.60 ins. and wall thickness 0.075 in. were moulded at 200°C for 15 mins. and rings 0.125 in. wide were subsequently cut from these cylinders and, after heating in glycerine at 180°C, were expanded on a PTFE mandrel of 1.98 in. diameter. The rings were cooled in cold water and then removed from the mandrel. The diameter immediately after removal was measured and the difference between this value and the mandrel diameter expressed as percentage of mandrel diameter is referred to as % snapback. The rings were kept in the expanded state for 24 hours and 1 week at 23°C and were then remeasured and the "holdout percentage" i.e. ratio of measured diameter at the time to snapback diameter calculated. Finally, all samples were shrunk by heating to 200°C for 10 minutes in an oil bath. The results were as given in Table I.

By way of a control experiment a similar mix was prepared except that no filler was present — this is referred to as Control No. 1 in Table I.

By way of further comparison, a similar mix was prepared using the uncoated filler in place of the silane coated filler. This is referred to as Control No. 2 in Table I.

For further comparison, a similar mix was prepared, but the coated filler was added to the hot blend of polyethylene and silicone polymer. This is referred to as Control No. 3 in Table I. The results in Table I clearly show the improvements to be obtained when the coated filler is blended with the non-silicone polymer before the latter is blended with the silicone polymer.

TABLE I

|  |  | Ex. 1 | Control No. 1 | Control No. 2 | Control No. 3 |
|---|---|---|---|---|---|
| Tensile strength psi |  | 1470 | 690 | 870 | 920 |
| " | (150°C) | 684 | — | 240 | 290 |
| " | (200°C) | 475 | — | 190 | 250 |
| Elongation at break % |  | 490 | 385 | 275 | 310 |
| " | (150°C) | 603 | — | 365 | 415 |
| " | (200°C) | 516 | — | 300 | 380 |
| 100 % modulus | (150°C) | 110 | — | 70 | 71 |
| " | (200°C) | 114 | — | 68 | 68.5 |
| Specific gravity |  | 1.21 | 1.20 | 1.21 | 1.21 |
| Dielectric strength volts/ 0.001 in. |  | 336 | 300 | 305 | 299 |
| Compatibility on moulding |  | satisfactory | bad lamination | bad lamination | some lamination |
| Snap back % |  | 9 | 15 | 12 | 12 |
| Holdout 1 day % |  | 99 | 94 | 96 | 95 |
| 7 days % |  | 99 | 90 | 91 | 95 |
| Recovery % (1 week in expanded state) |  | +100 | 96 | 98 | 99 |

+A value less than 100 indicates that complete recovery to original unexpanded diameter did not take place.

EXAMPLE 2

The following formulation was prepared in the manner described in Example 1.

| High Density Polyethylene (melt index 3.5; specific gravity 0.96) | 20 gms |
|---|---|
| Methyl phenyl vinyl silicone gum rubber | 70 gms |
| Coated Silica filler | 15 gms |
| Calcined ferric oxide | 0.5 gms |
| Triallyl Cyanurate | 0.2 gms |
| 2,5-dimethyl-2,5-di(tertiary butyl-poroxy) hexyne-3 | 0.2 gms |

The coated filler was the same as that used in Example 1.

Test plaques were moulded as described in Example 1. By way of comparison, a Control No. 4 formulation, containing all the ingredients except the coated filler was prepared. Similarly, a Control No. 5 formulation was prepared which contained untreated silica filler in place of the coated one.

The results obtained when the physical properties of test-plaques obtained from each of the three formulations were measured are given in Table II.

TABLE II

|  |  | Example 2 | Control No. 4 | Control No.5 |
|---|---|---|---|---|
| Tensile strength psi |  | 1425 | 650 | 790 |
| " | (150°C) | 495 | 136 | 215 |
| " | (200°C) | 356 | 168 | 187 |
| Elongation at break % |  | 660 | 300 | 290 |
| " | (150°C) | 950 | 600 | 937 |
| " | (200°C) | 760 | 660 | 810 |
| 100 % modulus | (150°C) | 63.5 | 42 | 38.5 |
| " | (200°C) | 61.5 | 34 | 42.0 |
| Specific Gravity |  | 1.23 | 1.21 | 1.23 |
| Dielectric strength volts/ 0.001 in. |  | 331 | 277 | 280 |
| Compatibility on moulding |  | satisfactory | severe fibrous lamination | bad lamination |

EXAMPLE 3

The following formulation was prepared as described in Example 1.

| Low density polyethylene (melt index : 3.0) | 20 gms |
|---|---|
| Hydrated silica | 10 gms |
| Vinyl trimethoxy silane | 2 gms |
| Methyl vinyl phenyl silicone rubber | 70 gms |
| Triallyl cyanurate | 0.2 gms |
| 2,5-dimethyl-2,5-di(tertiary butyl peroxy)-hexyne-3 | 0.2 gms |

The silicone rubber contained a reinforcing silica filler and was supplied by Dow Corning under the name DC 6565 U. The filler was thought to have a coating of octamethyl tetrasiloxane.

The hydrated silica had a specific surface area of 110 m$^2$/g (BET method) and an average particle size of approximately 20 m$\mu$. After addition of this filler to the polyethylene, the vinyl trimethohxy silane was added very slowly and the filler and polymer thoroughly mixed. The other components were added in the usual way.

Physical properties were determined on moulded test plaques and these are given in Table III. Further results were obtained with the same filler coated with vinyl trimethoxy silane by shaking the filler/silane mixture in a polyethylene bag for 1 week at room temperature.

TABLE III

|  | Example 3 (mill coated filler) | Example 3 (bag coated filler) | Control No. 2 |
|---|---|---|---|
| Tensile strength (psi) | 1260 | 1130 | 870 |
| " (150°C) | 684 | 583 | 240 |
| " (200°C) | 482 | 441 | 190 |
| Elongation at break % | 360 | 350 | 275 |
| " (150°C) | 658 | 640 | 365 |
| " (200°C) | 510 | 575 | 300 |
| 100 % modulus (150°C) | 125 | 117 | 70 |
| " (200°C) | 118 | 115 | 68 |
| Specific gravity | 1.21 | 1.21 | 1.21 |
| Dielectric strength (volts/ 0.001 in.) | 316 | 329 | 305 |
| Compatibility on moulding | satisfactory | satisfactory | bad lamination |

EXAMPLE 4

Similar results to those of Example 3 were obtained when a hydrated silica filler (surface area 140 m²/g) bag-treated with γ-methacryloxy propyltrimethoxy silane was used as the coated filler. The results were:

| Tensile strength (psi) | 1205 |
|---|---|
| Elongation at break % | 350 |
| Dielectric strength (Volts/ 0.001 in) | 305 |
| Compatibility on moulding | satisfactory. |

EXAMPLE 5

The following formulation was prepared.

| Copolymer of vinylidene fluoride and hexafluoropropylene | 50 gms |
|---|---|
| Methyl phenyl silicone rubber gum | 50 gms |
| Coated silica filler | 10 gms |
| Calcined ferric oxide | 5 gms |
| Dibasic lead fumarate | 5 gms |
| Calcined magnesium oxide | 5 gms |
| Triallyl cyanurate | 1.0 gms |
| 2,5-dimethyl-2,5-bis(tertiary butyl-peroxy)-hexyne-3 | 0.75 gms |

The vinylidene fluoride copolymer which was elastomeric was banded on a cold twin roll mill, the coated silica filler (identical to that in Example 1) was added, and the two components were thoroughly mixed for 15 minutes. The silicone rubber was then added and the milling and mixing continued for a further 25 minutes. The other ingredients were then added in the order given above. Test plaques 6 × 6 × 0.075 in. were pressed at 200°C for 15 minutes and then cured in an air oven at 220°C for 30 minutes.

By way of comparison, a control formulation No. 6 identical to the above formulation except that it contained a non-coated silica filler, was also prepared. Test plaques were also made from this formulation.

The results of tests carried out on the moulded plaques are given in Table IV.

TABLE IV

|  | Example 5 | Control No. 6 |
|---|---|---|
| Tensile strength psi | 1140 | 925 |
| Elongation at break % | 480 | 380 |
| Dielectric strength | 350 | 320 |
| Specific gravity | 1.52 | 1.53 |
| Tensile strength after 7 days at 220°C, psi | 810 | 1220 |
| Elongation at break after 7 days at 220°C, % | 350 | 140 |
| Compatibility on moulding | satisfactory | satisfactory- generally slight fibrous structure apparent |

EXAMPLE 6

Similar results were obtained when the vinylidene fluoride copolymer of Example 5 was replaced by 50 gms of an elastomeric terpolymer of vinylidene fluoride, tetrafluoroethylene and hexafluoropropylene or by 50 gms of an elastomeric copolymer of vinylidene fluoride and 1-hydropentafluoropropene (Technoflon SH). The results obtained from tests on the latter formulation and on a control composition (Control 6A) identical to the formulation except that it contained a non-coated filler are given in Table V. Ageing was carried out at 220°C.

TABLE V

|  |  | Example 6 | Control No. 6A |
|---|---|---|---|
| Tensile strength psi |  | 1025 | 950 |
| " | (aged 3 days) | 895 | 1250 |
| " | (aged 7 days) | 790 | 1420 |
| " | (aged 14 days) | 780 | 1500 |
| % Elongation at break |  | 460 | 350 |
| " | (aged 3 days) | 465 | 220 |
| " | (aged 7 days) | 335 | 100 |
| " | (aged 14 days) | 345 | 90 |
| Dielectric strength | (volts/0.001 in) | 320 | 300 |
| " | " (aged 14 days) | 330 | 320 |

EXAMPLE 7

The following formulation was prepared:

| Low density polyethylene (melt index : 3.0) | 20 gms |
|---|---|
| Coated Silica | 10 gms |
| Methyl phenyl silicone rubber | 70 gms |
| Calcined ferric oxide | 5 gms |

-continued

| | |
|---|---|
| Polymerized trihydroquinoline antioxidant | 0.5 gms |
| Triallyl cyanurate | 0.2 gms |
| 2,5-dimethyl-2,5-bis(tertiary butyl-peroxy)-hexyne-3 | 0.2 gms. |

The coated silica was the same as that used in Example 1. The silicone rubber was reinforced and was supplied by I. C. I. under the name E 361.

Plaques 5 × 2 × 0.25 ins. were prepared for testing according to ASTM D2303 which measures the tracking and erosion resistance of polymers by the Liquid Contaminant Inclined Plane. In this test, either the time to track at a fixed voltage or the voltage to initiate tracking is used as the test criteria, and the test is designed to represent service exposure of insulating materials under polluted conditions.

The time to track one inch at a fixed voltage was used in this case to show the beneficial effect of the fillers of the present invention on the tracking properties of the above polymers.

The contaminant used was 0.1 % ammonium chloride with 0.02 % glycerol-ethylene oxide condensate as non-ionic wetting agent. The resistivity of this solution was 385 ohms-cm at 23°C, and the rate of application was 0.30 cc/min.

By way of comparison, a Control No. 7 formulation identical to the above, except that an uncoated silica filler was used, was prepared and tested. The results were as follows:

TABLE V

| Material | Time to track 1 in. at 4 Kv (mins.) |
|---|---|
| Example 7 | 1050 |
| Control No. 7 | 76 |
| Example 8 | 960 |

The results show an improvement of approximately 14 times the time to track when the coated filler was used.

EXAMPLE 8

A formulation identical to Example 7 except that the filler was replaced by a silica aerogel coated with vinyl triethoxy silane. The coating was carried out by shaking the silane and silica aerogel in a sealed polythene bag at room temperature for one week. The time to track obtained with this filler is given in Table V.

EXAMPLES 9 to 12

| | |
|---|---|
| Silicone elastomer | 30 gms |
| Low density polyethylene | 30 gms |
| Ethylene-ethyl acrylate copolymer | 30 gms |
| Coated silica filler | 30 gms |
| Calcined ferric oxide | 5 gms |

-continued

| | |
|---|---|
| Polymerised trihydroquinoline antioxidant | 2 gms |
| Triallyl cyanurate | 1 gm |
| 2,5-dimethyl-2,5-bis(tertiary butyl-peroxy)-hexyne-3 | 0.5 gm |

The silicone elastomer was I. C. I. silicone E322/60, which is substantially polydimethyl siloxane reinforced with a treated silica filler. The ethylene-ethyl acrylate copolymer contained approximately 18 % ethyl acrylate.

The formulations were prepared by banding the polyethylene and ethylene-ethyl acrylate copolymer on a 2-roll mill at 120°C and then adding the coated silica filler (specified below) and mixing thoroughly. The silicone elastomer was then added and blended thoroughly into the above mixture. The ferric oxide and antioxidant were added and the mill rolls cooled to about 90°C when the remaining ingredients were added. The hide was stripped from the mill and cooled to room temperature. Test plaques 6 × 6 × 0.075 in. were pressed at 180°C for 15 minutes and the physical properties determined.

Control formulations containing uncoated aerogel silica of specific surface areas (BET method) of 150 and 200 sq. m/g were also prepared. These are designated Controls 8 and 9 respectively.

For

EXAMPLE 9 the silica filler specified above was coated with trimethyl chlorosilane and had a specific surface area before treatment of 150 sq. m/g.

For

EXAMPLE 10 the silica filler specified above was coated with β-(3,4-epoxy cyclohexyl)-ethyl trimethoxy silane, and had a specific surface area of 200 sq. m/g before treatment.

For

EXAMPLE 11 the silica filler specified above was coated with γ-glycidoxypropyl trimethoxy silane and had a specific surface area of 200 sq. m/g before treatment.

For

EXAMPLE 12 the silica filler was coated with N-bis(β-hydroxy ethyl) γ-amino-propyl triethoxy siloxane, and had a specific surface area of 200 sq. m/g before treatment. The physical properties are shown in Table VI:

TABLE VI

| | 23°C | | | 150°C | | |
|---|---|---|---|---|---|---|
| Material | Tensile Strength Kg/cm$^2$ | Elongation at break % | Dielectric strength Kv/cm | Tensile Strength Kg/cm$^2$ | 100 % Modulus Kg/cm$^2$ | Elongation at break % |
| Control 8 | 74 | 160 | 146 | 10.6 | 6.9 | 240 |
| Control 9 | 81.4 | 278 | 152 | 16.1 | 7.6 | 271 |
| Example 9 | 105 | 410 | 168 | 27.5 | 7.5 | 575 |
| Example 10 | 102 | 280 | 150 | 40.0 | 12.0 | 530 |
| Example 11 | 103 | 305 | 155 | 11.0 | 7.0 | 330 |
| Example 12 | 97 | 225 | 150 | 19.0 | 4.75 | 420 |

The tracking properties of the formulations were determined on plaques 5 × 2 × 0.25 in. pressed at 180°C for 15 minutes. The test used to measure these properties was a slight modification to the initial tracking voltage method of ASTM D2303-64T, using the following conditions in place of those normally specified:

| | |
|---|---|
| Power Supply: | 50 HZ |
| Contaminant: | 0.1 % ammonium chloride with 0.02 % glycerol-ethylene oxide condensate |
| Contaminant conductivity: | 330 ohm cms |
| Preparation of specimens: | thorough abrasion with 320 grit emery paper, samples not soaked 24 hours, no silver paint at bottom electrode. |

The voltage applied to the test samples was raised by 0.25 Kv every hour, regardless of whether tracking had commenced.

The results of the tests on the formulations of Example 9 to 12 and Controls 8 and 9 are given in Table VIII and show, together with the physical properties shown in Table VI, the beneficial results of using the compositions of the present invention.

EXAMPLES 13 to 15

| | |
|---|---|
| Silicone elastomer | 30 gms |
| Ethylene-ethyl acrylate copolymer | 30 gms |
| Ethylene-propylene-ethylidene norbornene terpolymer | 30 gms |
| Coated silica filler | 30 gms |
| Calcined ferric oxide | 5 gms |
| Polymerised trihydroquinoline antioxidant | 2 gms |
| iso-triallyl cyanurate | 2 gms |
| 2,5-dimethyl-2,5-bis(tertiary butyl-peroxy)-hexyne-3 | 2.5 gms. |

The silicone elastomer was I.C.I. Silicone E322/60. The formulations were prepared in similar fashion to Examples 9 to 12. The test plaques were pressed at 190°C for 10 minutes.

Control formulations were prepared containing uncoated silicas of specific surface areas 150 and 200 sq. m/g. These are designated Controls 10 and 11 respectively.
For

EXAMPLE 13, 13 the silica filler was coated with trimethyl chlorosilane before treatment and had a specific area before treatment of 150 sq. m/g.
For

EXAMPLE 14 the silica filler was coated with β-(3,4-epoxy-cyclohexyl)-ethyl trimethoxy silane and before treatment has a specific surface area of 200 sq. m/g.
For

EXAMPLE 15 the silica filler was coated with γ-glycidoxy-propyl trimethoxy silane, and before treatment had a specific surface area of 200 sq. m/g. The physical properties are shown in Table VII:

TABLE VII

| | 23°C | | | 150°C | | |
|---|---|---|---|---|---|---|
| Material | Tensile Strength Kg/cm² | Elongation at break % | Dielectric strength Kv/cm | Tensile Strength Kg/cm² | 100 % Modulus Kg/cm² | Elongation at break % |
| Control 10 | 76 | 265 | 134 | 17.5 | | 85 |
| Control 11 | 84 | 345 | 146 | 11.5 | 5.5 | 205 |
| Example 13 | 99 | 445 | 136 | 31.7 | 15.8 | 270 |
| Example 14 | 160 | 530 | 165 | 32.5 | 12.0 | 295 |
| Example 15 | 100 | 220 | 130 | 36.0 | 32.0 | 120 |
| Control 12 | 65 | 185 | 150 | 4.25 | 3.5 | 170 |
| Example 16 | 105 | 320 | 158 | 11.5 | 4.65 | 345 |

The tracking properties of the materials were measured as in Examples 9 to 12 and the results are given in Table VIII.

EXAMPLE 16

| | |
|---|---|
| Methyl phenyl silicone elastomer | 30 gms |
| Low density polyethylene (melt index 3.0 | 60 gms |
| Coated silica filler | 30 gms |
| Calcined ferric oxide | 5 gms |
| Polymerised trihydroquinoline antioxidant | 2 gms |
| Triallyl cyanurate | 1 gm |
| 2,5-dimethyl-2,5-bis(tertiary butyl-peroxy)-hexyne-3 | 5 gms |

The formulation was prepared in similar fashion to Example 1. The filler was silica coated with trimethyl chlorosilane and had a specific surface area before treatment of 130 sq. m/g. A control formulation containing an uncoated filler of the same surface area was also prepared, and this is designated Control 12. The results of physical property determinations measured on plaques pressed at 180°C for 15 minutes are given in Table VII.

The tracking properties were measured as in Examples 9 to 12 and are given in Table VIII.

TABLE VIII

| | Starting voltage Kv | Voltage to initiate tracking | Time to initial track from start of test (mins.) | Time to track 1″ (from start of test) (mins.) |
|---|---|---|---|---|
| Control 8 | 1.75 | 2.00 | 101 | 131 |
| Control 9 | 1.75 | 2.00 | 112 | 138 |
| Example 9 | 1.75 | 2.25 | 125 | 130 |
| Example 10 | 1.75 | 2.25 | 165 | 190 |
| Example 11 | 1.75 | 2.25 | 120 | 165 |
| Example 12 | 1.75 | 2.25 | 130 | 155 |
| Control 10 | 2.00 | 2.00 | 14 | 25 |
| Control 11 | 2.00 | 2.00 | 42 | 46 |
| Example 13 | 2.00 | 2.25 | 65 | 130 |

TABLE VIII-continued

|  | Starting voltage Kv | Voltage to initiate tracking | Time to initial track from start of test (mins.) | Time to track 1" (from start of test) (mins.) |
| --- | --- | --- | --- | --- |
| Example 14 | 2.00 | 2.25 | 75 | 165 |
| Example 15 | 2.00 | 2.25 | 65 | 125 |
| Control 12 | 1.50 | 1.50 | 61 | 75 |
| Example 16 | 1.50 | 1.75 | 95 | 110 |
| Control 13 | 1.50 | bad erosion at 2.25 | no tracking | burst into flames at 312 mins. |
| Control 14 | 1.50 | 1.75 | 66 | 183 |
| Example 17 | 1.50 | no tracking even at 3 Kv | no tracking | severe erosion after 394 mins |
| Example 18 | 1.50 | 1.75 | 105 | 201 |

EXAMPLES 17 to 18

| | Silicone elastomer E322/60 | 30 gms |
| --- | --- | --- |
| | Low density polyethylene | 30 gms |
| | Ethylene-ethyl acrylate copolymer | 30 gms |
| | Coated filler | 30 gms |
| | Calcined ferric oxide | 5 gms |
| | Polymerised tetrahydroquinoline antioxidant | 2 gms |
| | Triallyl cyanurate | 1 gm |
| | 2,5-dimethyl-2,5-bis(tertiary butyl-peroxy)-hexyne-3 | 0.5 gm |

The formulations were prepared as in the other Examples. Test plaques were cured at 190°C for 10 minutes.
For

EXAMPLE 17 the filler was a calcium-aluminium silicate containing, on a dry basis, 31 % by weight of calcium oxide and 4 % by weight of alumina, and having a surface area before coating of 228 m²/g. The silane coating was β-(3,4-epoxy cyclohexyl)-ethyl trimethoxy silane. A control experiment, reference Control No. 13, was carried out using the same filler without the silane coating.
For

EXAMPLE 18 the filler was hydrated calcium silicate having a surface area before treatment of approximately 44 m²/g, and treated with β-(3,4-epoxy cyclohexyl)-ethyl silane. A control experiment reference Control No. 14, was carried out using the same filler without the silane coating. The results of physical property tests on these compositions are given in Table IX and demonstrate the superior properties of the composition made according to the invention. The tracking properties of the materials of Examples 17 and 18 and Controls 13 and 14 are shown in Table VIII.

TABLE IX

| | 23°C | | | 150°C | | |
| --- | --- | --- | --- | --- | --- | --- |
| | Tensile Strength Kg/cm² | Elongation at break % | Dielectric strength Kv/cm | Tensile Strength Kg/cm² | 100 % Modulus Kg/cm² | Elongation at break % |
| Control 13 | 71.1 | 148 | 140 | 13.6 | 6.9 | 236 |
| Control 14 | 81.4 | 278 | 152 | 16.1 | 7.6 | 271 |
| Example 17 | 88.0 | 150 | 170 | 22.0 | 10.5 | 250 |
| Example 18 | 101 | 225 | 176 | 17.3 | 9.0 | 230 |

What is claimed is:

1. A process for the manufacture of a composition comprising a silicone polymer, a non-silicone polymer other than polytetrafluoroethylene and a chemically treated filler, the chemically treated filler being a filler comprising an inorganic silicone-containing compound containing the Si—O—Si group and having a specific surface area (measured by the BET method) of at least 40 square meters per gram, which filler has been treated with at least one silane having bonded to each silicon atom thereof at least one organic group bonding through a silicon-carbon bond, which process comprises:

a. blending said non-silicone polymer, said silane and said filler to form a blend of said non-silicone polymer and said treated filler; and blending the resulting blend with said silicone polymer.

2. The process of claim 1 wherein said filler is treated with said silane prior to said blending with said non-silicone polymer.

3. The process of claim 1 wherein the said non-silicone polymer is first blended with said filler and this blend is treated with said silane.

4. The process of claim 1 wherein said silicone polymer is selected from the group consisting of polydimethyl siloxane and a copolymer of dimethyl siloxane with up to 5 % by weight based on the weight of the dimethyl siloxane of methyl vinyl siloxane, and the non-silicone polymer is selected from the group consisting of a blend of an ethylene/ethyl acrylate copolymer and an ethylene/propylene/ethylidene norbornene terpolymer and a blend of low density polyethylene and an ethylene/ethyl acrylate copolymer.

5. The composition produced by the process of claim 1.

* * * * *